(12) United States Patent
Cicchetti et al.

(10) Patent No.: US 10,914,748 B2
(45) Date of Patent: Feb. 9, 2021

(54) ERYTHROCYTE-DERIVED EXTRACELLULAR VESICLES AS A BIOMARKER FOR CLINICALLY ASSESSING PARKINSON'S DISEASE

(71) Applicant: UNIVERSITÉ LAVAL, Québec (CA)

(72) Inventors: Francesca Cicchetti, Québec (CA); Eric Boilard, Québec (CA); Steve Lacroix, Lévis (CA); Isabelle St-Amour, Québec (CA)

(73) Assignee: Université Laval, Québec (CA)

( * ) Notice: Subject to any disclaimer, the term of this patent is extended or adjusted under 35 U.S.C. 154(b) by 0 days.

(21) Appl. No.: 15/699,904

(22) Filed: Sep. 8, 2017

(65) Prior Publication Data
US 2018/0067134 A1    Mar. 8, 2018

Related U.S. Application Data

(60) Provisional application No. 62/384,978, filed on Sep. 8, 2016.

(51) Int. Cl.
*G01N 33/68* (2006.01)

(52) U.S. Cl.
CPC ............... *G01N 33/6896* (2013.01); *G01N 2333/70503* (2013.01); *G01N 2333/70557* (2013.01); *G01N 2333/70589* (2013.01); *G01N 2333/70596* (2013.01); *G01N 2800/2835* (2013.01)

(58) Field of Classification Search
None
See application file for complete search history.

(56) References Cited

U.S. PATENT DOCUMENTS

| | | |
|---|---|---|
| 8,211,653 B2 | 7/2012 | Klass et al. |
| 9,128,101 B2 | 9/2015 | Halbert et al. |
| 2008/0220013 A1 | 9/2008 | Hochstrasser et al. |
| 2011/0151460 A1 | 6/2011 | Klass et al. |
| 2012/0178177 A1 | 7/2012 | Delerive et al. |
| 2014/0141986 A1 | 5/2014 | Spetzler et al. |
| 2014/0194319 A1 | 7/2014 | Skog et al. |
| 2015/0017660 A1 | 1/2015 | Ochiya |
| 2015/0168400 A1 | 6/2015 | Ichiki et al. |
| 2016/0011213 A1 | 1/2016 | Tofaris |

FOREIGN PATENT DOCUMENTS

| | | |
|---|---|---|
| CA | 2574727 A1 | 2/2006 |
| CA | 2610268 A1 | 12/2006 |
| CA | 2713909 A1 | 8/2009 |
| WO | 2009100029 A1 | 8/2009 |
| WO | 2014059052 A1 | 4/2014 |
| WO | 2014082083 A1 | 5/2014 |
| WO | 2015061634 A2 | 4/2015 |
| WO | 2015130956 A2 | 9/2015 |
| WO | 2015200851 A1 | 12/2015 |
| WO | 2018/145211 A1 | 8/2018 |

OTHER PUBLICATIONS

Yuana et al (Blood Rev 27: 31-39, 2013).*
Exocarta list of exosome markers, downloaded on Sep. 26, 2018, from <http://exocarta.org/exosome_markers>.*
Cell Sorting—Wikipedia, pp. 1-7, downloaded on Jul. 16, 2019 from https://en.wikipedia.org/wiki/Cell_sorting.*
Santana et al (Biomed Microdevices 16: 869-877, 2014).*
Aatonen, Maria T. et al., "Isolationn and characterization of platelet-derived extracellular vesicles", Journal of Extracellular Vesicles, 2014, vol. 3, pp. 1-15.
Ankarklev, Johan et al., "Uncovering the Role of Erythrocyte-derived Extracellular Vesicles in Malaria: From Immune Regulation to Cell Communication", Journal of Circulating Biomarkers, vol. 3, No. 3, pp. 1-11, 2014.
Emmanouilidou, Evangelia et al., "Cell-Produced α-Synuclein is Secreted in a Calcium-Dependent Manner by Exosomes and Impacts Neuronal Survival", The Journal of Neuroscience, May 19, 2010, vol. 30(20), pp. 6838-6851.
Fraser, Kyle B. et al., "LRRK2 secretion in exosomes is regulated by 14-3-3", Human Molecular genetics, 2013, vol. 22, No. 24, pp. 4988-5000.
Lacroix, R. et al., "Impact of pre-analytical parameters on the measurement of circulating microparticles: towards standardization of protocol", Journal of Thrombosis and Haemostasis, 2011, vol. 10, pp. 437-446.
Lamontagne-Proulx, J. et al., "Content of alpha-synuclein in erythrocyet-derived microvesicles: implications for Parkinson's disease", Program No. 41.14, Poster No. C48, 2015, Neuroscience Meeting Planner, Washington, DC: Society for Neuroscience, 2015. (Published online on Sep. 9, 2016).
Lötvall, Jan et al., "Minimal experimental requirements for definition of extracellular vesicles and their functions: a position statement from the International Society for Extracellular Vesicles", Journal of Extracellular Vesicles, 2014, vol. 3, pp. 1-6.
Martinez-Martin, Pablo et al., "Parkinson's disease severity levels and MDS-Unified Parkinson's Disease Rating Scale", ScienceDirect, Parkinsonism and Related Disorders, Elsevier Ltd., 2014, pp. 1-5.
Raposo, Graça et al., "Extracellular vesicles: Exosomes, microvesicles, and friends", The Rockefeller University Press, J. Cell Biol., 2013, vol. 200, No. 4, pp. 373-383.
Rousseau, Matthieu et al., "Detection and Quantification of Microparticles from Different Cellular Lineages Using Flow Cytometry. Evaluation of the Impact of Secreted Phospholipase A2 on Microparticle Assessment", Valery Combes, University of Sydney, Australia, Jan. 14, 2015, PLOS One, DOI:10.1371/journal.one.0116812, pp. 1-27.

(Continued)

*Primary Examiner* — Daniel E Kolker
*Assistant Examiner* — Aditi Dutt
(74) *Attorney, Agent, or Firm* — Hamilton, Brook, Smith & Reynolds, P.C.

(57) ABSTRACT

The present description relates to methods for clinically assessing Parkinson's disease in a subject using erythrocyte-derived extracellular vesicles (EEV) as a biomarker.

11 Claims, 7 Drawing Sheets
(7 of 7 Drawing Sheet(s) Filed in Color)

(56) References Cited

OTHER PUBLICATIONS

Shi, Min et al., "Plasma exosomal α-synuclein is likely CNS-derived and increased in Parkinson's disease", NIH Public Access, Acta Neuropathol, Nov. 2014, vol. 128(5), pp. 639-650.
Tomlinson, Paul R. et al., "Identification of distinct circulating exosomes in Parkinson's disease", Annals of Clinical and Translational Neurology, 2015, vol. 2(4), pp. 353-361.
Vella, Laura J. et al., "Focus on Extracellular Vesicles: Exosomes and Their Role in Protein Trafficking and Biomarker Potential in Alzheimer's and Parkinson's Disease", International Journal of Molecular Sciences, 2016, vol. 17, 173, pp. 1-20.
Werner, Cornelius J. et al., "Proteome analysis of human subtantia nigra in Parkinson's disease", Proteome Science, 2008, vol. 6:8, pp. 1-14.
Yanez-Mo, Maria et al., "Biological properties of extracellular vesicles and their physiological functions", Journal of Extracellular Vesicles, 2015, vol. 4, pp. 1-62.
Yang, Yue et al., "Cerebrospinal Fluid Particles in Alzheimer Disease and Parkinson Disease", HHS Public Access, J Neuropathol Exp Neurol., Jul. 2015, vol. 74(7), pp. 672-687.
Lamontagne-Proulx, J. et al., "Portrait of blood-derived extracellular vesicles in patients with Parkinson's disease," Neurobiology of Disease, vol. 124; 163-175 (2019).

\* cited by examiner

ERYTHROCYTE-DERIVED EXTRACELLULAR VESICLES AS A BIOMARKER FOR CLINICALLY ASSESSING PARKINSON'S DISEASE

RELATED APPLICATION(S)

This application claims the benefit of U.S. Provisional Application No. 62/384,978, filed on Sep. 8, 2016. The entire teachings of the above application are incorporated herein by reference.

BACKGROUND

Parkinson's disease (PD) is one of the most common neurodegenerative disorders affecting millions of people worldwide. Definite diagnosis for PD can only be made postmortem, for instance, by the characteristic accumulation of the protein alpha-synuclein into Lewy body inclusions in neurons. Currently, the diagnosis of PD is based on fitting observed symptoms and their severity into clinical rating scales such as the Unified Parkinson's Disease Rating Scale (UPDRS) or the Hoehn & Yahr scale. Current clinical assessments are subjective, however, and would benefit from improved methods of clinically assessing PD, particularly at early stages of the disease.

SUMMARY

The present description relates to Parkinson's disease. More particularly, the present description relates to the use of extracellular vesicles originating from erythrocytes as a biomarker for clinically assessing Parkinson's disease in a subject.

The present description stems from the surprising discovery that erythrocytes of Parkinson's disease (PD) subjects produce more extracellular vesicles (EV) than erythrocytes from corresponding control subjects, and that the level of erythrocyte-derived extracellular vesicles (EEV) strongly correlates with PD stage and treatment. In contrast, no significant differences between PD and control blood samples were observed in the number of EV originating from other cell types (e.g., platelets, endothelial cells, monocytes, granulocytes, and leukocytes), suggesting that the effect is specific for EV originating from erythrocytes. Furthermore, the increase in number of EEV and its strong correlation with PD stage was not observed in erythrocytes from Huntington's disease subjects, suggesting that these observations are specific for PD. Thus, the present description relates to the use of EEV as a biomarker for clinically assessing Parkinson's disease.

Accordingly, the present description may relate to the following aspects:

1. An in vitro method for clinically assessing Parkinson's disease in a human subject, said method comprising:
   (a) quantifying the level of erythrocyte-derived extracellular vesicles (EEV) in a blood sample from the subject; and
   (b) comparing the level of EEV to a suitable reference value indicative of the presence, stage and/or progression of Parkinson's disease, thereby clinically assessing Parkinson's disease in the subject.

2. The method of aspect 1, wherein said EEV are CD235a+ extracellular vesicles.

3. The method of aspect 1 or 2, wherein said EEV are TSG101+, Rabs+, CD9+, CD63+, CD81+, or any combination thereof.

4. The method of any one of aspects 1 to 3, wherein said blood sample is platelet-free-plasma.

5. The method of any one of aspects 1 to 4, wherein said EEV are between about 20 nm and about 1000 nm in diameter.

6. The method of any one of aspects 1 to 5, wherein said EEV are greater than about 100 nm in diameter.

7. The method of any one of aspects 1 to 6, wherein said EEV are quantified by flow cytometry, nanoparticle tracking (NTA), or electron microscopy.

8. The method of any one of aspects 1 to 7, wherein clinically assessing Parkinson's disease in the subject comprises diagnosing Parkinson's disease in the subject.

9. The method of any one of aspects 1 to 8, wherein clinically assessing Parkinson's disease in the subject comprises staging Parkinson's disease in the subject.

10. The method of any one of aspects 1 to 9, wherein clinically assessing Parkinson's disease in the subject comprises monitoring the progression of Parkinson's disease in the subject.

11. The method of aspect 10, wherein steps (a) and (b) are repeated on a further blood sample from the subject obtained at a later point of time.

12. Erythrocyte-derived extracellular vesicles (EEV) from a human subject's blood sample for use as a biomarker for clinically assessing Parkinson's disease in said subject.

13. Use of erythrocyte-derived extracellular vesicles (EEV) from a human subject's blood sample as a biomarker for clinically assessing Parkinson's disease is said subject.

14. The EEV of aspect 12, or the use of aspect 13, wherein said EEV are CD235a+ extracellular vesicles.

15. The EEV of aspect 12 or 14, or the use of aspect 13 or 14, wherein said EEV are TSG101+, Rabs+, CD9+, CD63+, CD81+, or any combination thereof.

16. The EEV of any one of aspects 12, 14 and 15, or the use of any one of aspects 13 to 15, wherein said EEV are between about 20 nm and about 1000 nm in diameter.

17. The EEV of any one of aspects 12, 14, 15 and 16, or the use of any one of aspects 13 to 16, wherein said EEV are greater than about 100 nm in diameter.

18. The EEV of any one of aspects 12 and 14 to 17, or the use of any one of aspects 13 to 17, wherein said EEV are present in platelet-free plasma.

19. The EEV of any one of aspects 12 and 14 to 18, or the use of any one of aspects 13 to 18, wherein said clinical assessment comprises diagnosing Parkinson's disease in the subject.

20. The EEV of any one of aspects 12 and 14 to 19, or the use of any one of aspects 13 to 19, wherein said clinical assessment comprises staging Parkinson's disease in the subject.

21. The EEV of any one of aspects 12 and 14 to 20, or the use of any one of aspects 13 to 20, wherein said clinical assessment comprises monitoring the progression of Parkinson's disease in the subject.

GENERAL DEFINITIONS

Headings, and other identifiers, e.g., (a), (b), (i), (ii), etc., are presented merely for ease of reading the specification and claims. The use of headings or other identifiers in the specification or claims does not necessarily require the steps or elements be performed in alphabetical or numerical order or the order in which they are presented.

The use of the word "a" or "an", when used in conjunction with the term "comprising" in the claims and/or the specification may mean "one" but it is also consistent with the meaning of "one or more", "at least one", and "one or more than one".

The term "about" is used to indicate that a value includes the standard deviation of error for the device or method being employed to determine the value. In general, the terminology "about" is meant to designate a possible variation of up to 10%. Therefore, a variation of 1, 2, 3, 4, 5, 6, 7, 8, 9 and 10% of a value is included in the term "about". Unless indicated otherwise, use of the term "about" before a range applies to both ends of the range.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, un-recited elements or method steps.

Other objects, advantages and features of the present description will become more apparent upon reading of the following non-restrictive description of specific embodiments thereof, given by way of example only with reference to the accompanying drawings.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

In the appended drawings.

DETAILED DESCRIPTION

Figure 1A:
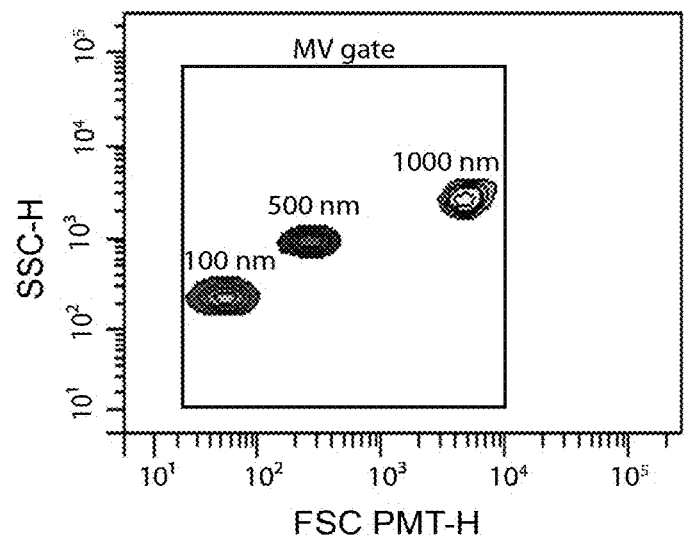
FIGS. 1A-1F show controls for flow cytometry in order to optimize the detection of the extracellular vesicles (EV). (A) To properly set the EV gate, fluorescent silica beads of 100 nm (Red), 500 nm (Blue) and 1000 nm (Yellow) were acquired on a flow cytometer Canto II modified with a FSC-PMT small particles option. The EV gate was used throughout the experiments. (B) Serial dilutions (1, 2, 4 and 10) of erythrocyte-derived EV (EEV) to confirm the linearity of the quantification. (C) FSC-PMT/SSC gates of platelet-free plasma (PFP) stained with annexin V and respective fluorochrome-conjugated antibodies directed against erythrocyte (CD235a+), endothelial (CD31+/CD41−)/platelets (CD41+) and leukocytes (CD14+CD45+, monocytes; CD15+CD45+, granulocytes)-derived EV. (D) Treatment with the ion chelator EDTA inhibited the binding of annexin V to phosphatidylserine. (E) Minimal background was observed using antibodies in absence of PFP. This background was subtracted from all subsequent EV quantifications. (F) EV sensitivity to 0.5% Triton™ was assessed. Abbreviations: AnnV, annexin V; FSC PMT-H, forward scatter photomultiplier; PBS, phosphate buffered saline; PFP, platelet free plasma; SSC-H, side scatter.
Figure 1B:
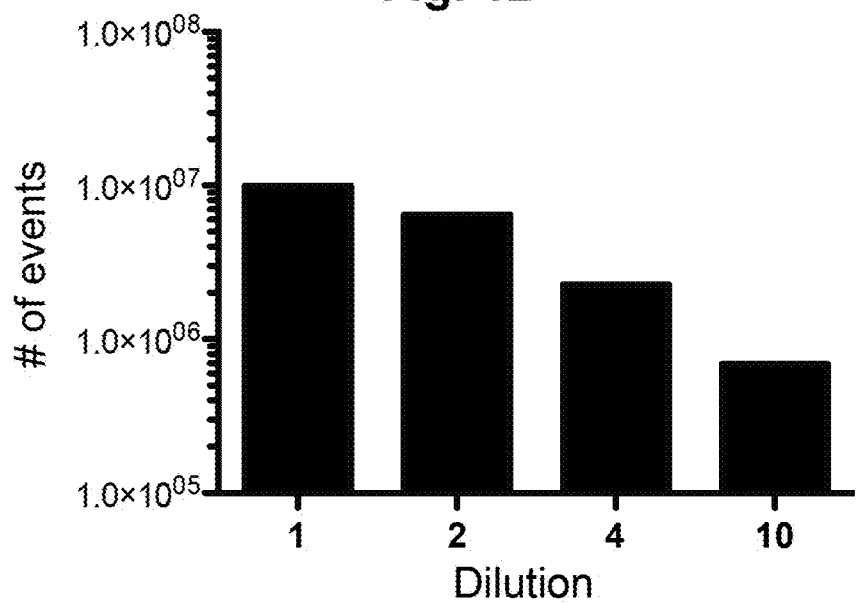
Figure 1C:
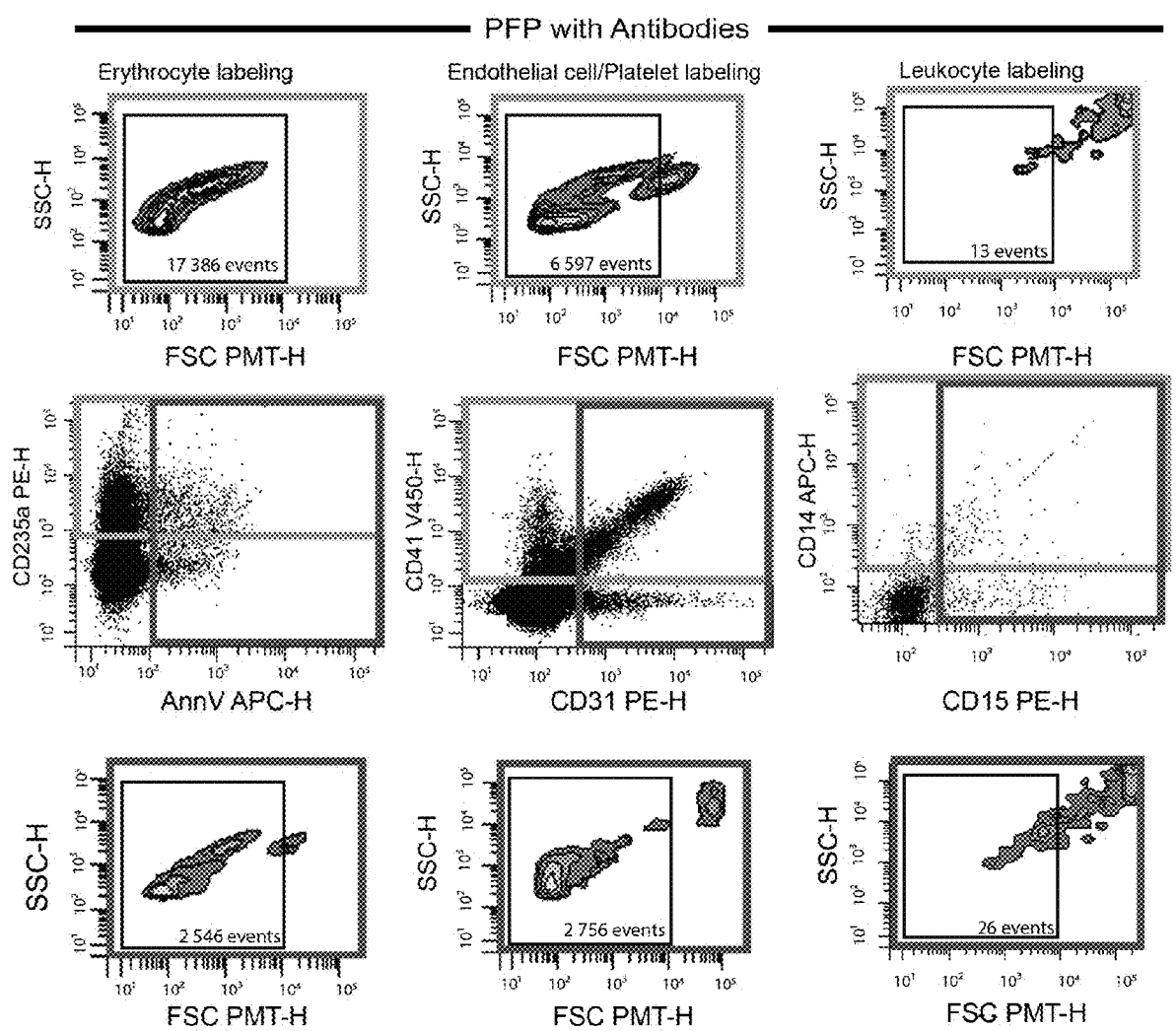
Figure 1D:
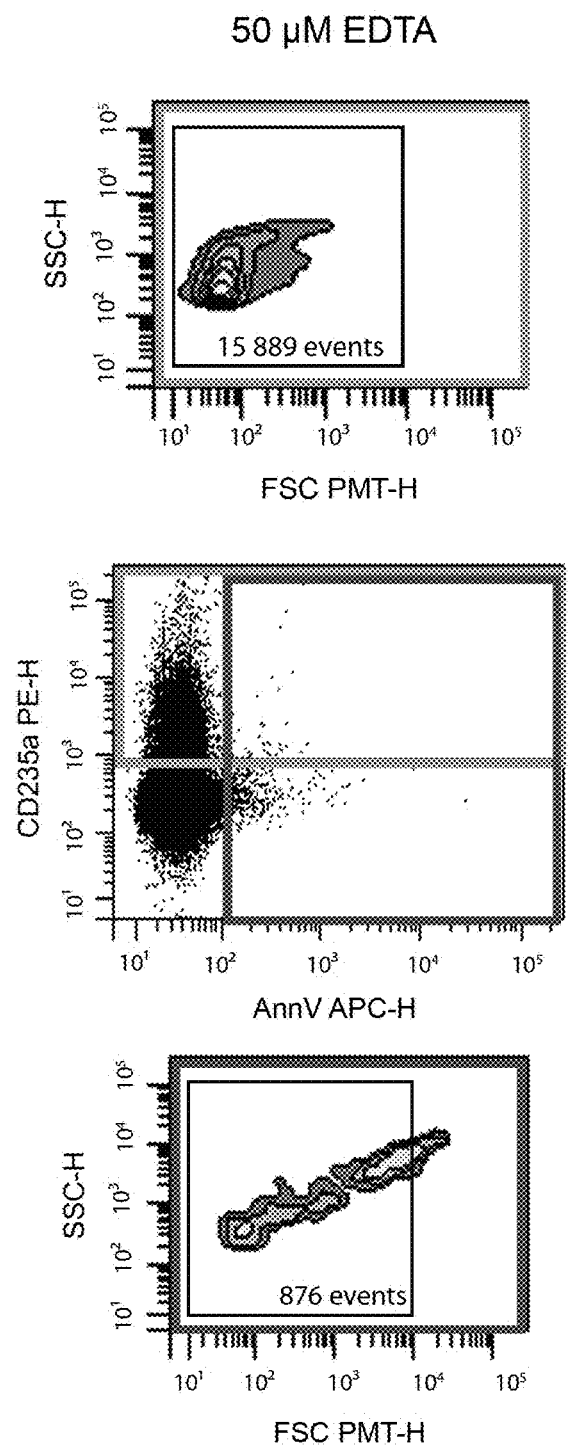
Figure 1E:
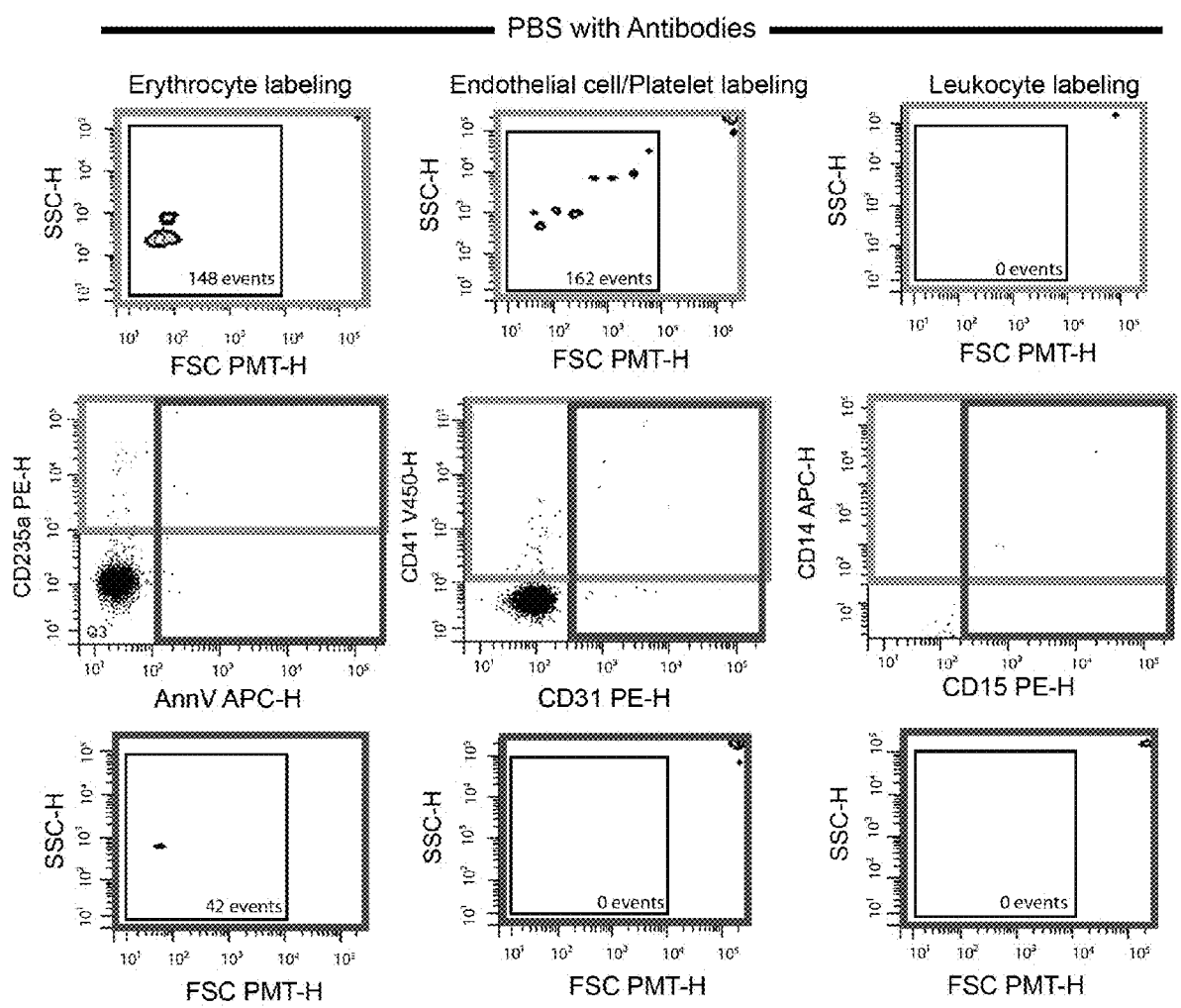
Figure 1F:
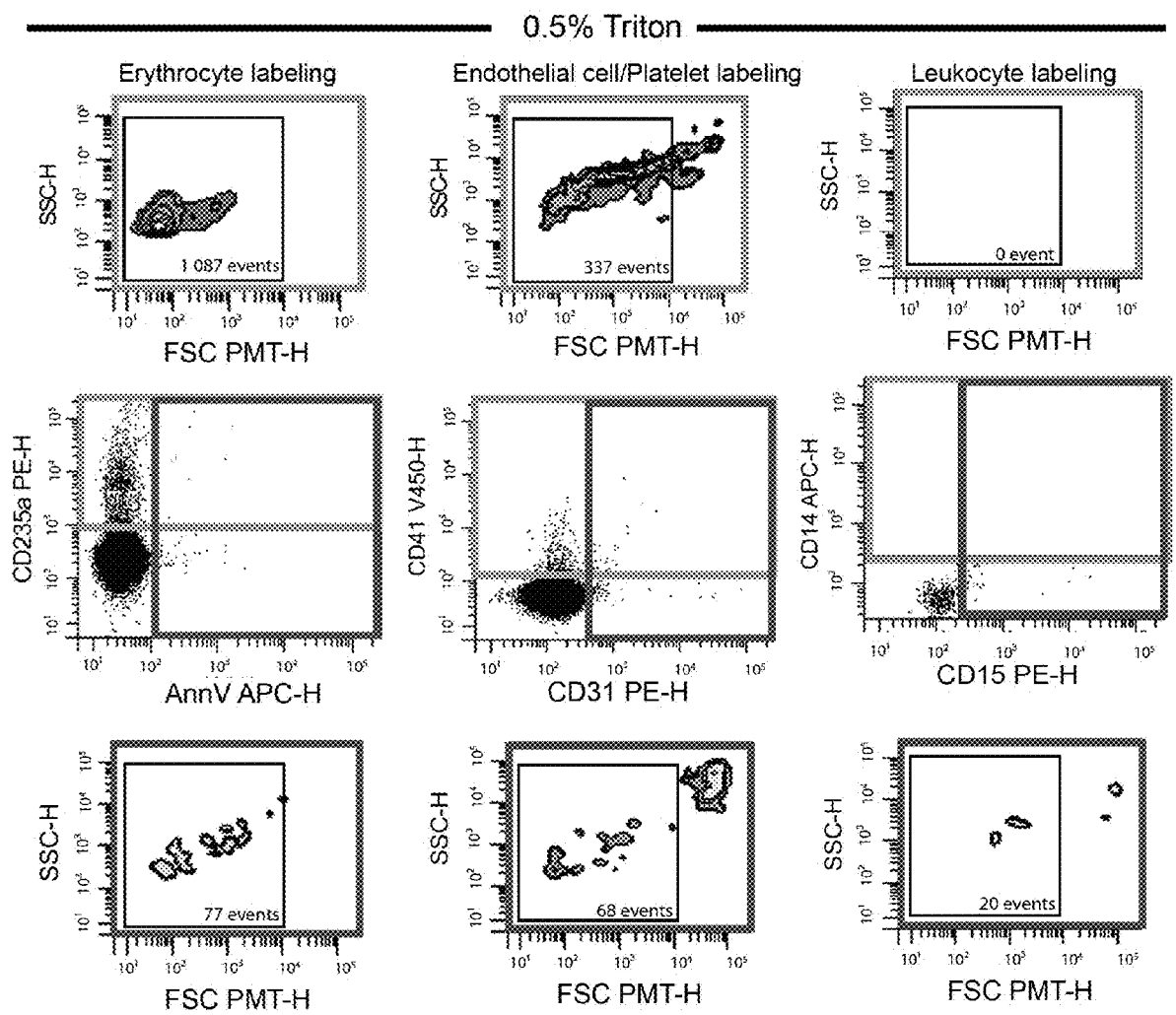

The present description stems from the surprising discovery that erythrocytes of Parkinson's disease (PD) subjects produce more extracellular vesicles (EV) than erythrocytes from corresponding control subjects, and that the level of erythrocyte-derived extracellular vesicles (EEV) strongly correlates with PD stage and PD treatment. This effect was not observed for EV originating from other cell types (e.g., platelets, endothelial cells, monocytes, granulocytes, and leukocytes). Furthermore, the increase in number of EEV and its strong correlation with PD stage was not observed in erythrocytes from Huntington's disease subjects, suggesting that these observations are specific for PD. Thus, the present description relates to the use of EEV as a biomarker for clinically assessing Parkinson's disease.

In some aspects the present description relates to a method for clinically assessing Parkinson's disease in a human subject using extracellular vesicles originating from erythrocytes as a biomarker.

As used herein, the expression "clinically assessing" or "clinical assessment" in the context of PD refers to an evaluation of a subject's PD state, which may or may not occur in a clinical setting, and which may or may not be performed by a health care professional. For example, clinically assessing may comprise screening and/or diagnosing PD in a subject having or suspected of having PD, staging a subject's PD, monitoring the progression of PD in a subject, monitoring the effect of PD medication, or any combination thereof.

As used herein, the term "biomarker" refers to a molecular indicator that is associated with a particular pathological or physiological state. For example, the expression "Parkinson's disease biomarker" or "PD biomarker" refers to a molecular indicator that is associated with the presence, stage, and/or progression of PD in a subject.

As used herein, the expression "extracellular vesicles" (EV) refers to subcellular membrane vesicles found in the extracellular environment (e.g., bodily fluids) that originate from cells, and which range in size from about 20 nm to about 1000 nm. EV may comprise exosomes, microvesicles (MV), multivesicular endosomes (MVE), or vesicles produced by apoptotic bodies, or any combination thereof, as well as other types of extracellular vesicles. Whereas the majority of the circulating EV that are efficiently detected by flow cytofluorometric assays are likely to be MV, we do not completely exclude the potential contribution of larger exosomes or vesicles produced by apoptotic bodies. In some embodiments, the EV of the present description comprise vesicles between about 30, 40, 50, 60, 70, 80, 90, or 100 nm to about 500, 600, 700, 800, 900, or 1000 nm in size. In some embodiments, the EV of the present description comprise vesicles between greater than 100 nm to 1000 nm in size. In some embodiments, the EV of the present description comprise vesicles between 150 nm to 1000 nm in size. All EV are composed of membrane proteins and lipids, as well as cytoplasmic components of the cell from which they originate, such as mRNA and miRNA, organelles or infectious particles (e.g., prions, virus). A variety of methods may be used to determine the origin of EV. For example, cell surface markers (e.g., with immunolabeling and/or flow cytometry techniques) may be used to identify, enrich/purify/isolate, and/or quantify EV according to their cell of origin. Examples of such markers include: CD235a+ (erythrocytes), CD31+/CD41− (endothelial cells), CD41+ (platelets), CD45+ (leukocytes), CD45+CD14+ (monocytes), and CD45+CD15+ (granulocytes). Of particular interest for the present description are markers that are present in (or specific for) EEV that may be used to identify, enrich/purify/isolate, and/or quantify EEV from other types of EV. Examples of such FFV markers include endosome or membrane-bonding proteins such as TSG101 and Rabs (enriched in exosomes), tetraspanins such as CD9, CD63 and CD81 (enriched in exosomes), golgi and mitochondrial proteins (enriched in MVs and absent in exosomes) (Lotvall et al., 2014).

As used herein, the expression "[market]+ EV" or "[marker]–positive" refers to the presence or detectability of that marker in an EV population of interest, regardless of whether that marker is actually detected (e.g., using an immunolabel). Conversely, the expression "[marker]– EV" or "[marker]–negative EV" refers to the absence or lack of detectability of that marker in an EV population of interest, regardless of whether that marker is actually detected (e.g., using an immunolabel). For example, the expression "CD235+ EV" or "CD235a-positive EV" means EV that comprise the marker CD235a (Glycophorin A).

In some embodiments, the method of the present description may comprise identifying, enriching/purifying/isolating, and/or quantifying EEV in a blood sample from the subject. As used herein, the terms "enriched", "purified", "isolated" and the like, refer to either removing contaminants from a biological sample and/or increasing the concentration of an analyte of interest in the sample, to an extent that is not found in nature. In some embodiments, identifying, enriching/purifying/isolating, and/or quantifying EEV may be performed by flow cytometry, or other methods such as nanoparticle tracking (NTA), biochemical approaches and semi-quantitative electron microscopy approaches. In some embodiments, the quantification of EEV may be expressed as a relative value by normalizing the number of EEV (e.g., in terms of the total number of erythrocytes).

In some embodiments, the methods of the present description may further comprise comparing the level of EEV to a suitable reference value indicative of the presence, stage and/or progression of Parkinson's disease, thereby clinically assessing Parkinson's disease in the subject.

As used herein, the expression "reference value" means a control value or range of values corresponding to a known level or range of EEV associated with the presence, stage and/or progression of Parkinson's disease. In some embodiments, for example where the number of EEV has previously been measured in a blood sample from a subject, the reference value may be a value corresponding to the same subject's previous reading (e.g., a baseline). The term "suitable" in the expression "suitable reference value" reflects the observations reported herein that the number of EEV in blood samples from PD subjects may vary depending on, for example, factors which may also affect the EV and/or EEV levels. For example, it is reported herein that a subject's EEV levels may be affected by whether or not the subject is being treated for their PD symptoms, the number of PD treatments being taken by the subject, whether the subject has or previously had cancer, whether the subject has or previously had diabetes, or whether the subject is taking anti-inflammatory medication.

In some aspects, the blood samples may be processed to obtain platelet-free plasma.

In some aspects, the present invention relates to erythrocyte-derived extracellular vesicles (EEV) from a human subject's blood sample for use as a biomarker for clinically assessing Parkinson's disease in said subject. In some aspects, the present invention relates to the use of erythrocyte-derived extracellular vesicles (EEV) from a human subject's blood sample as a biomarker for clinically assessing Parkinson's disease is said subject.

Other objects, advantages and features of the present description will become more apparent upon reading the following non-restrictive description of specific embodiments thereof, given by way of example only with reference to the accompanying drawings.

The present description refers to a number of documents, the contents of which are herein incorporated by reference in their entirety.

EXAMPLES

Example 1—Methods 1.1 Participant Recruitment and Ethic Statement

Human blood was obtained from two cohorts of participants. The first cohort was composed of Parkinson's disease (PD) patients and Controls, and the second cohort was composed of Huntington's disease (HD) patients and Controls. The demographics for both cohorts are shown in Table 1. For the two cohorts, the Controls were recruited amongst the caregivers, spouses, family and friends of the patients. Institutional review boards approved this study (CHU de Québec-Université Laval, #A13-2-1096; CHUM, #14.228; Cambridge Central Regional Ethics Committee, REC #03/303; and Cambridge University Hospitals Foundation Trust Research and Development department, R&D #A085170) in accordance with the Declaration of Helsinki, and written informed consent was obtained from all participants. On the day of the blood collection, every participant filled in a questionnaire on health issues and medication.

Of note, participants excluded from the present EEV-related analyses included those with diabetes and those suffering or having suffered from cancer, because we observed a significant PD-independent increase in EEV concentration in the platelet-free plasma of these participants. Furthermore, PFP samples with elevated free hemoglobin (>45 000 ng/mL), potentially due to hemolysis at blood collection, were also excluded from EEV-related analyses.

TABLE 1

Participant demographics

Parkinson's disease (PD) cohort

| | | PD Patients-Stages of disease | | | | |
|---|---|---|---|---|---|---|
| | Ctrl | Unknown | Mild | Moderate | Severe | P value |
| n | 37 | 7 | 12 | 33 | 8 | |
| Age | 66.8 | 69.8 | 66.7 | 71.1 | 75.0* | 0.04 |
| Gender F (M) | 18 (19) | 1 (6) | 6 (6) | 16 (17) | 0 (8) | 0.05 |

TABLE 1-continued

Participant demographics

| Disease severity | | | | | | | | |
| --- | --- | --- | --- | --- | --- | --- | --- | --- |
| Hoehn & Yahr (n) | | | 1 ± 0.3 (12) | 2 ± 0.2 (33) | 3 ± 0.5 (8) | | <0.0001 | |
| UPDRS (n) | | | 38 ± 11 (6) | 52 ± 19 (17) | 73 ± 20 (6) | | 0.02 | |
| ACE (n) | | | 96 ± 4 (6) | 92 ± 7 (17) | 84 ± 14 (6) | | 0.13 | |
| MMSE (n) | | | 29 ± 2 (7) | 29 ± 1 (19) | 26 ± 3 (6) | | 0.01 | |
| BDI (n) | | | 3 ± 2 (6) | 4 ± 2 (17) | 13 ± 7 (4) | | 0.03 | |
| Comorbidities | | | | | | | | |
| Asthma | 3 | 1 | 1 | 5 | 0 | | 0.71 | |
| Hypertension | 10 | 1 | 2 | 10 | 3 | | 0.76 | |
| Diabetes | 2 | 0 | 0 | 1 | 2 | | 0.10 | |
| Cancer | 5 | 0 | 3 | 4 | 1 | | 0.64 | |
| Allergies | 2 | 0 | 2 | 6 | 2 | | 0.28 | |
| Depression | 3 | 1 | 2 | 1 | 2 | | 0.29 | |
| Hypercholesterolemia | 5 | 0 | 1 | 6 | 1 | | 0.73 | |

Huntington's disease (HD) cohort

| | | | HD Patients-Stages of disease | | | | | |
| --- | --- | --- | --- | --- | --- | --- | --- | --- |
| | Ctrl | Pre-HD | Stage 1 | Stage 2 | Stage 3 | Stage 4 | Stage 5 | P value |
| n | 55 | 11 | 15 | 13 | 12 | 10 | 2 | |
| Age | 55.0 | 37.5 | 53.1 | 54.2 | 58.3 | 58.1 | 55.5 | 0.02 |
| Gender F (M) | 31 (22) | 6 (5) | 5 (10) | 4 (9) | 8 (4) | 7 (3) | 1 (1) | 0.26 |
| Disease severity | | | | | | | | |
| UHDRS (n) | | 2.7 (11) | 15.7 (14) | 34.5 (11) | 42.9 (12) | 55.9 (10) | 67.5 (2) | <0.001 |
| TFC (n) | 13 (16) | 13 (11) | 12.5 (15) | 7.8 (13) | 4.3 (12) | 1.6 (10) | 0 (2) | <0.001 |
| CAG (n) | 28.3 (3) | 41.1 (10) | 42.3 (13) | 42.6 (12) | 43.7 (7) | 44.3 (7) | | <0.001 |
| BDS (n) | | 206 (10) | 337 (13) | 356 (12) | 442 (7) | 465 (7) | | <0.001 |
| Comorbidities | | | | | | | | |
| Asthma | 0 | 0 | 1 | 0 | 0 | 0 | 0 | 0.65 |
| Hypertension | 4 | 1 | 2 | 1 | 1 | 2 | 0 | 0.92 |
| Diabetes | 3 | 1 | 1 | 1 | 1 | 1 | 0 | 0.99 |
| Cancer | 0 | 0 | 0 | 0 | 0 | 0 | 0 | |
| Allergies | 3 | 0 | 2 | 2 | 0 | 0 | 0 | 0.33 |
| Depression | 8 | 1 | 1 | 3 | 6 | 4 | 1 | 0.0497 |
| Hypercholesterolemia | 8 | 1 | 1 | 0 | 0 | 1 | 0 | 0.32 |

Abbreviations:
ACE, Addenbrooke's cognitive examination;
BDI, Beck depression inventory;
BDS, Burden of Disease Score;
CAG, Trinucleotide repeat;
MMSE, Mini-Mental State Examination;
UHDRS, Unified Huntington's Disease Rating Scale;
TFC, Total Function Capacity.

1.2 Preparation of Platelet-Free Plasma (PFP) and Extracellular Vesicle (EV) Labeling Citrated blood was centrifuged twice for 15 minutes at 2500 g at room temperature. Platelet-free plasma (PFP) was harvested and stored at −80° C. within 2 hours of collection following guidelines suggested by Lacroix and colleagues (Lacroix et al., 2012).

For all experiments, diluted annexin-V buffer (BD Pharmingen, Mississauga, ON, Canada) and phosphate buffered saline (PBS) were filtered on 0.22 μm pore size membranes. To quantify the EV according to their cell of origin, the following surface markers were used: CD235a+ (erythrocytes), CD31+/CD41− (endothelial cells), CD41+ (platelets), CD45+ (leukocytes), CD45+CD14+ (monocytes), and CD45+CD15+ (granulocytes), with or without annexin-V staining. PFP (5 μL) was incubated with Phenylalanyl-prolyl-arginyl Chloromethyl Ketone (PPACK) (Calbiochem, Etobicoke, ON, Canada) for 5 minutes, followed by a 30-minute incubation with antibodies and annexin-V, all at room temperature. The following antibodies were purchased at BD Pharmingen and used throughout the experiments: FITC-conjugated mouse anti-human CD235a (clone GA-R2 (HIR2), 1/20), PE-conjugated mouse anti-human CD31 (clone WM59, 1/100), V450-conjugated mouse anti-human CD41a (clone HIPS, 1/20), APC mouse anti-human CD14 (clone M5E2, 1/10), PE-conjugated mouse anti-human CD15 (clone HI98, 1/50), V450-conjugated mouse anti-human CD45 (clone HI30, 1/33), V450- and PerCP-CyTM5.5-conjugated annexin-V (1/33 and 1/10, respectively).

1.3 Flow Cytometry Quantification

For EV quantification, we used a FACS Canto II Special Order Research Product equipped with a forward scatter (FSC) coupled to a photomultiplier tube (FSC-PMT). Flow cytometer performance tracking was carried out daily using the BD cytometer setup and tracking beads (BD Biosciences, San Jose, Calif., USA). The size of the EV was determined using fluorescent silicone beads of 100, 500 and 1000 nm. Controls and optimization of the detection method are presented in FIGS. 1A-1F. The settings for the EV detection were determined as described previously (Rousseau et al., 2015) using a threshold of 200 for SSC. Between PD and RD analyses, the blue laser had to be replaced for maintenance issues and therefore laser settings were reassessed. For FSC-PMT, the assigned voltage was 363 (PD) and 160 (HD) Volts. For SSC, the assigned voltage was 407 (PD) and 300 (HD) Volts. All other parameters were set between 450 and 500 Volts. The acquisition of EV was performed at low speed with an approximate rate of 10 µL/min. To determine background noise level, antibody mixes were incubated in absence of PFP sample and unlabeled PFP was used as a negative control.

1.4 Statistical Analyses

All statistical analyses were performed using "The Statistics and Machine Learning Toolbox" provided by MathWorks™ under the MATLAB™ platform. The version used was MATLAB®R2015a. The analysis included the scatter plot, the classical least-squares linear regression model, the R-squared and p values, as well as Pearson's goodness-of-fit model. Interval cut-off values were determined using a loop program developed in MATLAB™. Regression diagnostics, including residual behaviour and homoscedastivity, were also obtained with the same Toolbox.

Example 2—Results

The cohorts studied here included Parkinson's disease (PD) (n=60) and Huntington's disease (HD) patients (n=52) of all stages (see Example 1.1), as well as their respective age- and sex-matched healthy controls (n=37; n=55, respectively). The demographics for both cohorts are shown in Table 1. Full blood counts (erythrocytes, lymphocytes, platelets, leukocytes, monocytes, neutrophils) and C-reactive protein quantification were obtained for all participants, but they did not reveal any differences between groups (data not shown). Similarly, the hematocrit, the mean corpuscular hemoglobin, as well as the mean corpuscular volume values were similar between PD and control groups (data not shown).

2.1 PD Patients Exhibit a Disease-Specific Increase in Erythrocyte-Derived EV

Platelet-free plasma (PFP) and extracellular vesicles (EV) were labeled and quantified according to their cell of origin for all participants, as described in Examples 1.2 and 1.3. Results are summarized in Table 2A (PD patients and controls) and Table 2B (HD patients and controls).

As shown in Table 2A, no significant differences between PD patient and control samples were observed in the number of EV originating from platelets, endothelial cells, monocytes, granulocytes, and leukocytes. Similarly, as shown in Table 2B, no significant differences between HD patient and control samples were observed in the concentrations EV originating from these same cell types.

Interestingly, a significant increase in erythrocyte-derived EV in patients with PD was observed, as compared to the control group (see values highlighted in black in Table 2A). This increase in erythrocyte-derived EV in patients with PD was disease-specific, as the same effect was not observed in erythrocyte-derived EV in patients with HD (Table 2B).

TABLE 2A

Quantification of extracellular vesicles (EV) derived from different cell types of PD patients and controls

| Cell type | Markers | Units | CTRL n | CTRL Mean | CTRL SEM | PD n | PD Mean | PD SEM | P value |
|---|---|---|---|---|---|---|---|---|---|
| Platelets | CD41+PS− | ×10$^3$/µL | 37 | 7.88 | 1.68 | 59 | 10.3 | 1.33 | 0.27 |
| | CD41+PS+ | | 37 | 15.2 | 3.20 | 59 | 17.9 | 2.53 | 0.51 |
| | CD41+CD31+ | | 37 | 1.51 | 0.69 | 59 | 1.99 | 0.54 | 0.59 |
| | CD41+ total | | 37 | 23.1 | 4.62 | 59 | 28.2 | 3.66 | 0.38 |
| | EV CD41+/platelet | | 35 | 0.106 | 0.021 | 57 | 0.125 | 0.016 | 0.49 |
| Endothelial cells | CD31+CD41−PS− | ×10$^3$/µL | 37 | 15.8 | 8.04 | 59 | 11.7 | 6.37 | 0.75 |
| | CD31+CD41−PS+ | | 37 | 0.91 | 0.13 | 59 | 0.92 | 0.10 | 0.96 |
| | CD31+CD41− total | | 37 | 16.7 | 8.03 | 59 | 12.6 | 6.36 | 0.75 |
| Monocytes | CD45−CD14+PS− | ×10$^3$/µL | 37 | 1.70 | 0.30 | 59 | 1.62 | 0.24 | 0.85 |
| | CD45−CD14+PS+ | | 37 | 1.20 | 4.00 | 59 | 5.84 | 3.17 | 0.50 |
| | CD45+CD14+PS− | | 37 | 0.16 | 0.04 | 59 | 0.14 | 0.03 | 0.74 |
| | CD45+CD14+PS+ | | 37 | 0.60 | 0.79 | 59 | 1.47 | 0.63 | 0.59 |
| | CD14+ total | | 37 | 3.66 | 4.88 | 59 | 9.06 | 3.87 | 0.60 |
| | EV CD14+/monocyte | | 35 | 7.08 | 1.99 | 57 | 9.16 | 1.56 | 0.41 |
| Granulocytes | CD45−CD15+PS− | ×10$^3$/µL | 37 | 12.3 | 7.96 | 59 | 16.7 | 6.30 | 0.92 |
| | CD45−CD15+PS+ | | 37 | 2.21 | 0.77 | 59 | 1.39 | 0.61 | 0.47 |
| | CD45+CD15+PS− | | 37 | 0.55 | 0.36 | 59 | 1.15 | 0.29 | 0.20 |
| | CD45+CD15+PS+ | | 37 | 1.01 | 0.30 | 59 | 1.25 | 0.24 | 0.56 |
| | CD15+ total | | 37 | 16.0 | 8.83 | 59 | 20.6 | 6.99 | 0.91 |
| | EV CD15+/granulocyte | | 35 | 3.70 | 0.64 | 57 | 3.16 | 0.50 | 0.53 |
| Leukocytes | CD45+ total | ×10$^3$/µL | 37 | 10.4 | 2.21 | 59 | 13.8 | 1.75 | 0.26 |
| Erythrocytes | CD235a+PS− | ×10$^3$/µL | 36 | 18.2 | 46.5 | 59 | 32.0 | 36.3 | 0.04 |
| | CD235a+PS+ | | 36 | 0.22 | 0.07 | 59 | 0.29 | 0.05 | 0.70 |
| | CD235a+ total | | 36 | 18.4 | 47.0 | 59 | 32.3 | 36.7 | 0.04 |
| | EV CD235a+/erythrocyte | | 34 | 0.0039 | 0.011 | 57 | 0.0069 | 0.008 | 0.04 |

Abbreviations:
CD235a, glycophorin A;
EV, extracellular vesicle;
PD, Parkinson's disease;
PS, phosphatidylserine.

TABLE 2B

Quantification of extracellular vesicles (EV) derived from different cell types of HD patients and controls

| Cell type | Markers | Units | CTRL n | CTRL Mean | CTRL SEM | HD pre-manifest n | HD pre-manifest Mean | HD pre-manifest SEM | HD it | HD Mean | HD SEM | P value |
|---|---|---|---|---|---|---|---|---|---|---|---|---|
| Platelets | CD41+PS− | x | 54 | 9.2 | 2.2 | 10 | 4.3 | 1.3 | 50 | 6.1 | 1.0 | 0.78 |
| | CD41+PS+ | $10^3/\mu L$ | 54 | 19.3 | 4.8 | 10 | 7.1 | 2.0 | 50 | 12.4 | 2.4 | 0.74 |
| | CD41+ total | | 54 | 28.4 | 6.9 | 10 | 11.4 | 3.2 | 50 | 18.6 | 3.4 | 0.70 |
| | EV CD41+/platelet | | 53 | 0.12 | 0.03 | 10 | 0.05 | 0.02 | 48 | 0.08 | 0.01 | 0.34 |
| Endothelial cells | CD31+CD41−PS− | x | 54 | 1.4 | 0.3 | 10 | 0.6 | 0.2 | 50 | 1.2 | 0.2 | 0.31 |
| | CD31+CD41−PS+ | $10^3/\mu L$ | 54 | 0.68 | 0.16 | 10 | 0.25 | 0.06 | 50 | 0.46 | 0.09 | 0.59 |
| | CD31+CD41− total | | 54 | 2.1 | 0.4 | 10 | 0.8 | 0.2 | 50 | 1.7 | 0.3 | 0.26 |
| Monocytes | CD45−CD14+PS− | x | 54 | 3.4 | 1.1 | 10 | 1.6 | 0.2 | 51 | 1.6 | 0.1 | 0.91 |
| | CD45−CD14+PS+ | $10^3/\mu L$ | 54 | 1.8 | 0.3 | 10 | 0.8 | 0.3 | 51 | 1.5 | 0.2 | 0.14 |
| | CD45+CD14+PS− | | 54 | 0.18 | 0.07 | 10 | 0.069 | 0.016 | 51 | 0.056 | 0.008 | 0.34 |
| | CD45+CD14+PS+ | | 54 | 0.62 | 0.12 | 10 | 0.24 | 0.06 | 51 | 0.55 | 0.14 | 0.12 |
| | CD14+ total | | 54 | 6.0 | 1.3 | 10 | 2.6 | 0.4 | 51 | 3.7 | 0.4 | 0.08 |
| | EV CD14+/monocyte | | 53 | 12.3 | 2.5 | 10 | 5.7 | 0.6 | 48 | 8.0 | 1.0 | 0.13 |
| Granulocytes | CD45−CD15+PS− | x | 54 | 1.2 | 0.1 | 10 | 1.2 | 0.3 | 51 | 1.5 | 0.2 | 0.33 |
| | CD45−CD15+PS+ | $10^3/\mu L$ | 54 | 0.12 | 0.04 | 10 | 0.18 | 0.08 | 51 | 0.22 | 0.11 | 0.33 |
| | CD45+CD15+PS− | | 54 | 0.20 | 0.05 | 10 | 0.07 | 0.02 | 51 | 0.15 | 0.04 | 0.64 |
| | CD45+CD15+PS+ | | 54 | 0.25 | 0.05 | 10 | 0.13 | 0.06 | 51 | 0.20 | 0.04 | 0.39 |
| | CD15+ total | | 54 | 1.7 | 0.2 | 10 | 1.6 | 0.4 | 51 | 0.20 | 0.3 | 0.67 |
| | EV CD15+/granulocyte | | 53 | 0.41 | 0.04 | 10 | 0.42 | 0.13 | 48 | 0.50 | 0.08 | 0.75 |
| Leukocytes | CD45+ total | x $10^3/\mu L$ | 54 | 33.4 | 2.7 | 10 | 31.6 | 5.3 | 51 | 31.7 | 2.4 | 0.88 |
| Erythrocytes | CD235a+PS− | x | 54 | 15.2 | 2.0 | 10 | 10.3 | 3.5 | 51 | 14.1 | 1.4 | 0.16 |
| | CD235a+PS+ | $10^3/\mu L$ | 54 | 1.1 | 0.2 | 10 | 0.4 | 0.2 | 51 | 1.1 | 0.1 | 0.04 |
| | CD235a+ total | | 54 | 16.4 | 2.0 | 10 | 10.7 | 3.5 | 51 | 15.3 | 1.5 | 0.09 |
| | EV CD235a+/erythrocyte | | 54 | 0.0035 | 0.0005 | 10 | 0.0023 | 0.0008 | 50 | 0.0033 | 0.0003 | 0.11 |

Abbreviations:
CD235a glycophorin A;
EV extracellular vesicle;
HD, Huntington's disease;
PS, phosphatidylserine.

Figure 2A:
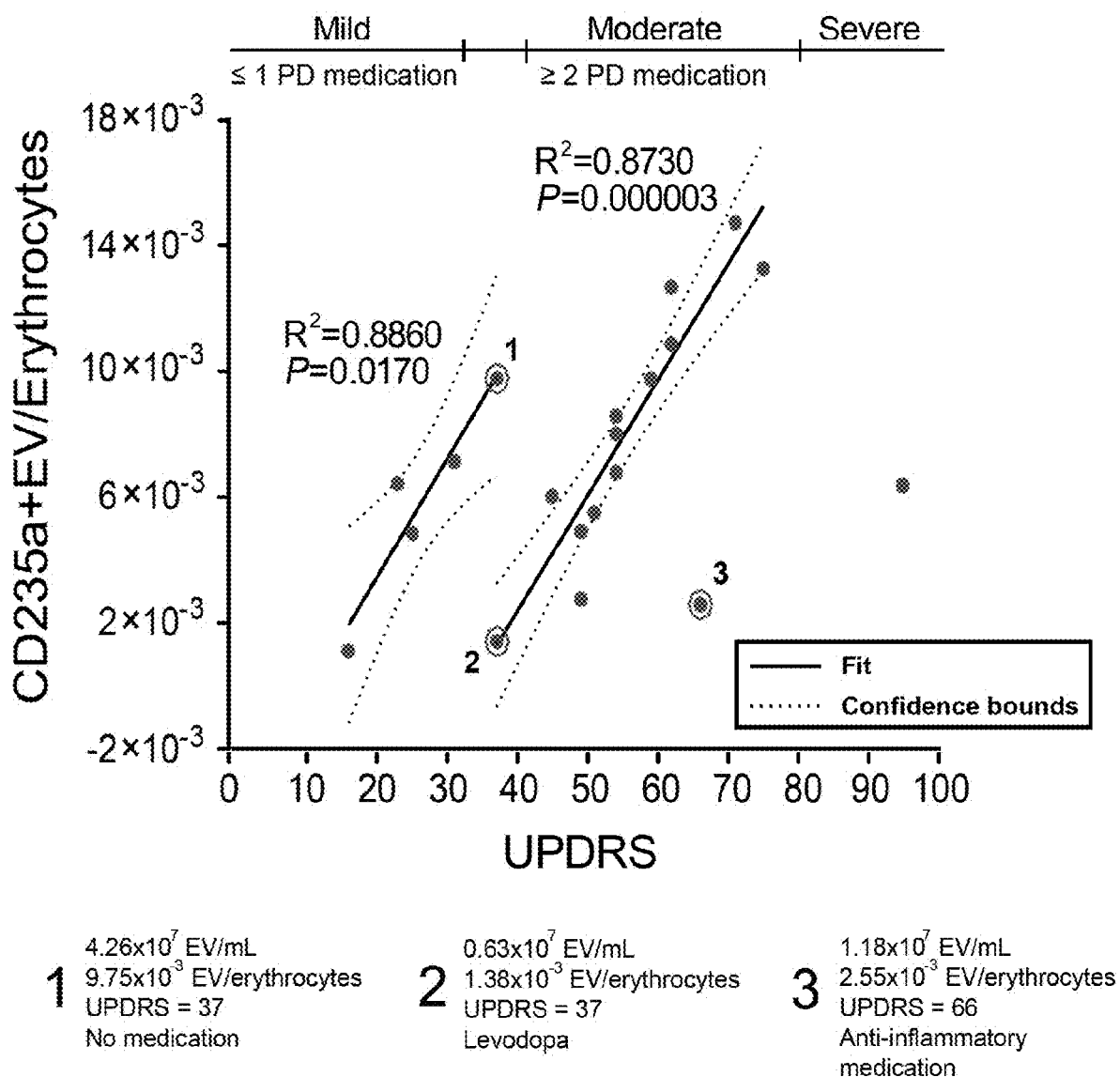
FIG. 2A shows the correlations between the number of erythrocyte-derived extracellular vesicles (EEV; expressed as CD235a+ EV/total number of erythrocytes) and the Unified Parkinson's Disease Rating Scale (UPDRS) of subjects (n=20). Subjects identified as "1" and "2" both presented with the same UPDRS score of 37, but subject "1" was not receiving any treatment for their PD symptoms, while subject "2" was being treated with levodopa. Subject "3" presented with a UPDRS score of 66, but was taking anti-inflammatory medications to manage arthritis.

2.2 Increase in Erythrocyte-Derived EV in PD Patient Samples Correlates with PD Progression and PD Treatment To evaluate its suitability as a potential biomarker for monitoring PD progression, we examined correlations between the number of erythrocyte-derived EV (EEV) and two different PD staging systems: the Hoehn & Yahr scale, and Unified Parkinson's Disease Rating Scale (UPDRS). Strikingly, this analysis revealed strong correlations between the number of erythrocyte-derived EV and PD stage/progression, when using either of these PD rating scales. As shown in FIG. 2A, strong correlations (correlations exceeding 0.8) were observed between the number of erythrocyte-derived EV (expressed as CD135a+EV/total number of erythrocytes) and patient UPDRS score, and thus PD stages. Similar strong correlations were also observed using the Hoehn & Yahr scale (data not shown), although the UPDRS is being presented because of its greater sensitivity and the recent publications validating this approach (see Martinez-Martin et al., 2015). By stratifying the PD patients according to their disease severity and/or treatment, it was observed that "mild" PD patients with a UPDRS score lower than 35 and taking ≤1 PD medication, showed an increased number of EEV during disease evolution (correlation=0.886). A very similar pattern (correlation=0.873) was observed for "moderate" PD patients with UPDRS scores between 35 and 75 and taking ≥2 PD medications, with almost all data points falling within the statistical confidence bounds. Of note, one patient presenting with a UPDRS score of 66 exhibited a relatively low count of EEV, but this patient was taking anti-inflammatory medications to manage his arthritis, which may explain this result (see FIG. 2A, patient "3"). A lack of available data precluded a similar analysis for patients presenting with severe PD (UPDRS scores higher than 75).

Interestingly, two patients presenting with the same UPDRS score of 37 had very different numbers of EEV. The patient receiving treatment for their PD symptoms (see FIG. 2A, patient "2") exhibited much a lower number of EEV than another patient having the same UPDRS score but who was not receiving any treatment for their PD symptoms (see FIG. 2A, patient "1").

Figure 2B:
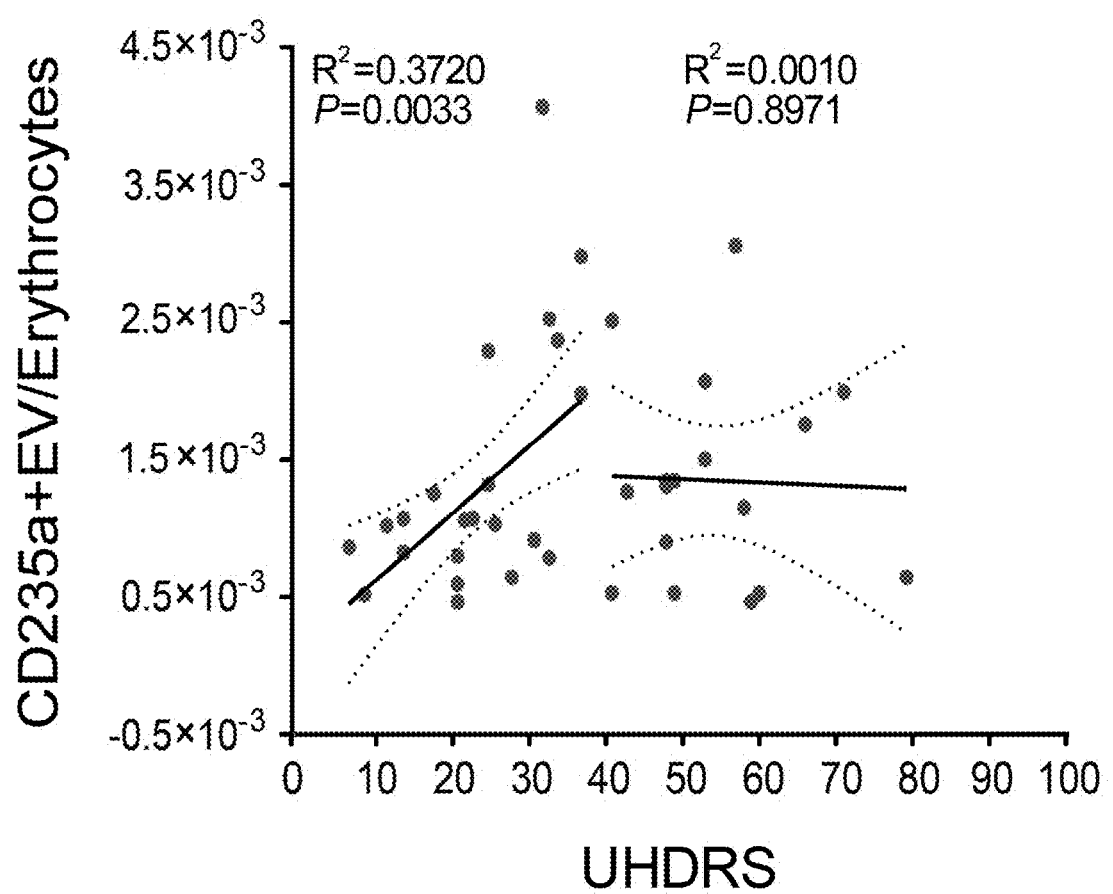
FIG. 2B shows the results of a similar analysis as in FIG. 2A, but performed on Huntington's disease subjects (n=42) using the Unified Huntington's Disease Rating Scale (UHDRS). The numbers of EEV are expressed as CD235a+ EV/total number of erythrocytes.

The above correlations observed with respect to the number of EEV in PD patients was found to be disease-specific, since a similar analysis performed in HD patients failed to reveal the same strong correlations (see FIG. 2B).

We have thus identified at least two distinct groups of PD patients with highly significant correlations to the number of EV derived from erythrocytes, which relates to PD stage and/or PD treatment (FIG. 2A). Strikingly, these correlations appear to be specific to PD, as similar correlations were not observed in the cohort of HD patients (of varying degrees of severity) in which we performed identical analyses (FIG. 2B).

REFERENCES

Lacroix et al, *Journal of Thrombosis and Haemostasis* (2012), 10:437-446.
Lotvall et al., *J Extracell Vesicles* (2014), 3:26913.
Martinez-Martin et al., *Parkinsonism & related disorders* (2015). 21(1):50-4.
Rousseau et al., *PLoS One* (2015), 10(1):e0116812.

What is claimed is:

1. A method for preparing a clinical human blood sample, said method comprising:
   (a) identifying a human subject as having or suspected of having Parkinson's disease;
   (b) obtaining a blood sample comprising erythrocyte-derived extracellular vesicles (EEVs) from the human subject having or suspected of having Parkinson's disease;
   (c) processing said blood sample by separating EEVs having a diameter of greater than 100 nm from EEVs having a diameter of less than 100 nm, thereby obtaining a processed blood sample comprising EEVs of diameter greater than 100 nm;
   (d) quantifying the level of EEVs of diameter greater than 100 nm in the processed blood sample enriched sample.

2. The method of claim 1, wherein said EEV are CD235a+ extracellular vesicles.

3. The method of claim 1, wherein said EEV are TSG101+, Rabs+, CD9+, CD63+, CD81+, or any combination thereof.

4. The method of claim 1, wherein said blood sample is platelet-free-plasma.

5. The method of claim 1, wherein said EEV quantified in (d) are between 100 nm and 1000 nm in diameter.

6. The method of claim 1, wherein said EEV are quantified by flow cytometry, nanoparticle tracking (NTA), or electron microscopy.

7. The method of claim 1, wherein steps (a) to (d) are repeated on an additional blood sample from the same subject obtained at a later point of time.

8. The method of claim 1, wherein the processed blood sample enriched for extracellular vesicles of diameter greater than 100 nm has a higher number of EEVs of diameter greater than 100 nm than a corresponding processed blood sample from a non-Parkinson's disease subject.

9. The method of claim 1, wherein the quantifying in (d) further comprises separating the EEVs from non-EEVs in the processed blood sample.

10. The method of claim 1, wherein the blood sample is from a Parkinson's disease subject having a Unified Parkinson's Disease Rating Scale (UPDRS) score lower than 35.

11. The method of claim 1, wherein the blood sample is from a Parkinson's disease subject having a UPDRS score between 35 and 75.

* * * * *